United States Patent [19]

Auphan

[11] 4,106,348

[45] Aug. 15, 1978

[54] DEVICE FOR EXAMINATION BY MEANS OF ULTRASONIC VIBRATIONS

[75] Inventor: Michel Joseph Auphan, Paris, France

[73] Assignee: U.S. Philips Corporation, New York, N.Y.

[21] Appl. No.: 764,585

[22] Filed: Feb. 1, 1977

Related U.S. Application Data

[63] Continuation of Ser. No. 550,957, Feb. 19, 1975.

[30] Foreign Application Priority Data

Feb. 20, 1974 [FR] France .................................. 74 05718

[51] Int. Cl.² ............................................ G01N 29/04
[52] U.S. Cl. .......................................... 73/624; 73/626
[58] Field of Search ............. 73/67.7; 340/5 MP, 1 R; 358/112

[56] References Cited

U.S. PATENT DOCUMENTS 3,577,772  5/1971  Perilhou et al. ..................... 73/67.7

Primary Examiner—Richard C. Queisser
Assistant Examiner—John P. Beauchamp
Attorney, Agent, or Firm—Frank R. Trifari; Jack E. Haken

[57] ABSTRACT

A device for ultrasonic examination, comprising a flat mosaic of a row of transmission transducers and a number of rows of receive transducers which are symmetrically arranged with respect thereto. The device furthermore comprises means for applying actuation pulses to one transmission transducer at a time, and means for enabling receive transducers in the time interval following each actuation pulse, and for at the same time displaying on an image display device an image of a section of the examined body in a plane perpendicular to the plane of the mosaic and through the line of transmission transducers.

3 Claims, 4 Drawing Figures

DEVICE FOR EXAMINATION BY MEANS OF ULTRASONIC VIBRATIONS

This is a continuation of application Ser. No. 550,957, filed Feb. 19, 1975.

The invention relates to a device for the examination of a section of a body situated in an analysis plane P by means of ultrasonic vibrations, the said device comprising a number of transmission transducers having a direction of transmission situated in the plane P and being arranged in a line situated in the plane P, and a number of direction-dependent receive transducers which are arranged such that they are capable of receiving echo signals formed by mirror reflection from interfaces in the body being examined, the receive directions of the receive transducers being situated in at least one plane P' which is perpendicular to the line of transmission transducers.

French Patent Specification No. 1,497,496 describes a method of and a device for the ultrasonic examination of reflective surfaces of substantially different curvature, for example, surfaces of living tissue. This device can notably be used for the examination of the topography of organs inside the human body. The said Patent Specification describes a method whereby ultrasonic waves are transmitted to the organ to be examined by a transmitter, part of the reflected waves being intercepted by a receiver. This transmitter comprises a series of approximately point-shaped transmission transducers which successively transmit pulses which constitute a narrow beam, the said beams together constituting a substantially flat transmission area. The receiver comprises a series of approximately pointshaped receive transducers which constitute a receive area which is approximately flat and which intersects the transmission area. A few receive transducers receive the ultrasonic waves reflected in the receive area, and the line of intersection of the transmission area and the receive area can be shifted in the plane of the relevant section of the organ to be examined.

The positions of the various echo points are calculated on the one hand on the basis of the coordinates of the transmission transducers and the receive transducers which contribute to the formation of an echo signal, and on the basis of the delay time of the ultrasonic wave between transmission transducer and receive transducer on the other hand. In this device the scanning is mechanically effected.

The invention has for its object to realize the advantages of the known device without mechanical scanning.

To this end, the device according to the invention is characterized in that the receive transducers are connected to terminals, the receive transducers connected to one common terminal together constituting a receive element, each receive element extending along a line perpendicular to the plane P such that a number of planes P' exist, each of which comprises at least one receive element, further means being provided for actuating the transmission transducers one at a time by way of an ultrasonic transmission actuation pulse, and also means being provided for actuating successively determined receive transducers in the time interval following each transmission actuation pulse, an image display device being provided which comprises a display screen and means for forming an image on the display screen, the said imaging means being coupled to the means for actuating the receive transducers such that each echo signal which reaches an actuated receive transducer causes the formation of an image element in a location on the display screen such that the image elements together constitute an image of the reflective surfaces of the body examined which intersect the plane P.

The invention will be described in detail hereinafter with reference to the drawing.

FIG. 1 shows the basic arrangement of the transmitters and the receive structure according to the invention.

FIG. 2 diagrammatically shows the practical arrangement of the elements of FIG. 1 and an embodiment of the circuits cooperating therewith.

Figure 1:
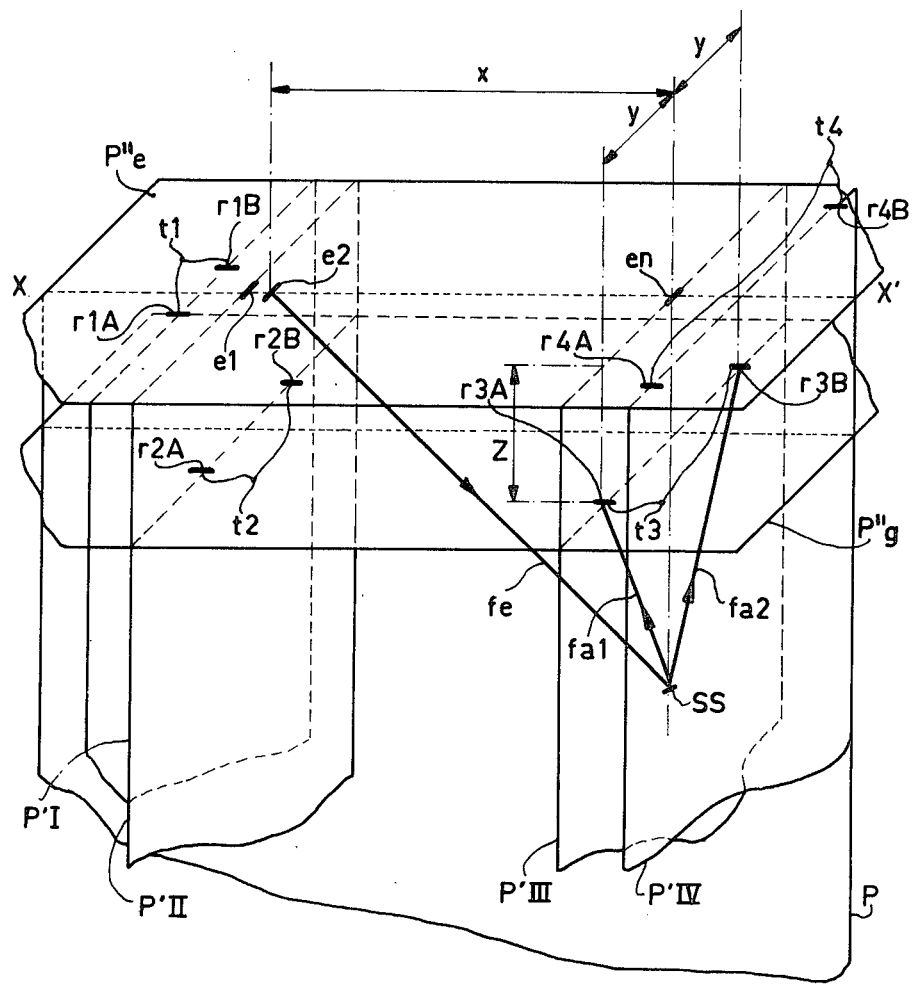

In a plane P, coinciding with the plane of the drawing of FIG. 1, there are arranged $n$ ultrasonic transmission transducers $e1 \ldots en$. Each of these transmission transducers is arranged such that its direction of transmission is situated in the plane P, which means that the (generally fan-shaped) beam transmitted by the transmission transducer propagates in different directions in this plane, and notably that the axis of this beam is situated in the plane P.

FIG. 1 also shows part of the receive structure cooperating with the said $n$ transmission transducers. This structure comprises a number of terminals, only four of which are shown, i.e. $t1, t2, t3, t4$. Each terminal is connected to a receive element; each receive element forms part of a group of receive elements situated in a plane P' which is perpendicular to the plane P and to the row of transmission transducers. There are $m$ groups of $n$ receive elements each ($m \times n$ receive elements), so also $m$ planes P', four of which are shown in FIG. 1 (P'I, P'II, P'III, P'IV), which contain the groups of receive elements connected to the said terminals $t1 \ldots t4$. Each receive element is also situated in a plane P'' which is perpendicular to the planes P and P'; the receive elements shown are situated in only two plans P'': the receive elements connected to the terminals $t1$ and $t4$ are situated in the plane P''$e$ which also contains the row of transmission transducers, and the receive elements connected to the terminals $t2$ and $t3$ are situated in the plane P''$g$.

FIG. 1 shows that each receive element actually comprises two receive transducers which are symmetrically arranged with respect to the plane P. For example, the receive transducers $r1A$ and $r1B$ form the receive element connected to terminal $t1$, etc. This structure offers advantages which will be described hereinafter.

At the line of intersection of the plane P and the plane P'III there is shown an interface $ss$ of the structure of a body having a section which is situated in the plane P and which is to be examined. If the transmission transducer $c2$ is actuated at a given instant T, thus causing the transmission of a pulse-shaped ultrasonic beam $fe$, this beam will propagate in the analysis plane P in the indicated direction. The beam $fe$ encounters the surface $ss$, thus causing an echo signal which is reflected in the plane P'III in a direction which encloses an angle with the line of intersection of the planes P and P'III; this angle has a value and a direction which are dependent on the angle of inclination of the interface $ss$. Two possible echo beams $fa1$ and $fa2$ are shown in FIG. 1. It appears to be advantageous to provide two receive transducers which are symmetrical with respect to the plane P and which are connected to one terminal: at a given angle of inclination of the interface ss an echo signal is then received, regardless of the direction of the interface ss with respect to the plane P.

If it is assumed that:

c is the velocity of the sound in the medium between e2 and ss, x is the distance between the transmission transducer and the plane P'III, y is the distance between the receive transducers r3A and r3B, connected to the terminal t3, and the plane P, z is the distance between the plane P"g and the plane P"e, and if it is assumed that at the instant t an echo signal is received on the terminal t3, the distance h between the surface ss and the line of the plane P comprising the row of transmission transducers can be determined by trigonometry:

$$h = f(c, t, x, y, z) \quad (1)$$

Figure 2:
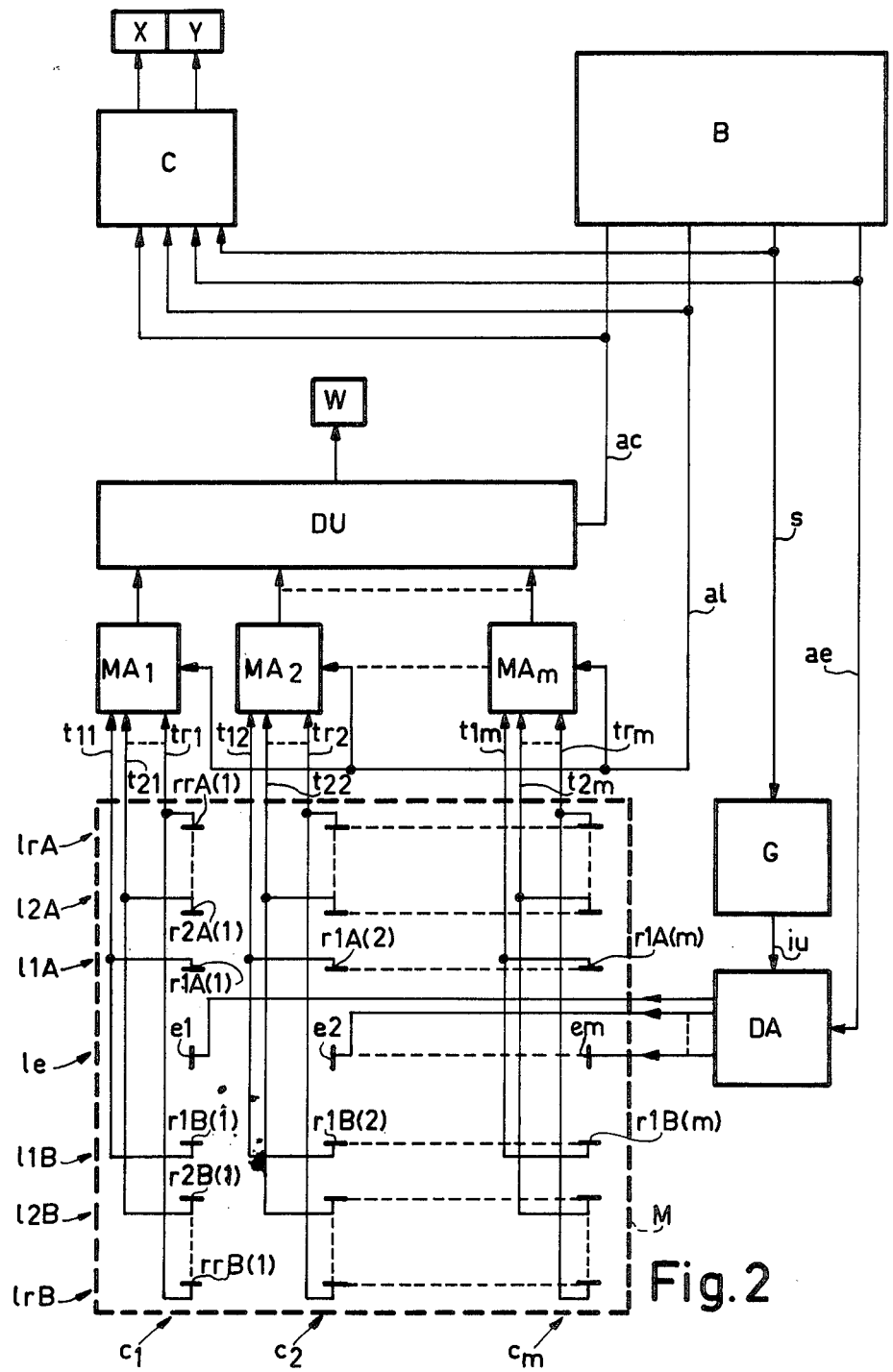

As is also shown in FIG. 2, the receive structure is preferably and most simply formed by a flat mosaic M which is situated in the plane P"e which contains the row of transmission transducers. In that case the formula (1) does not contain any terms which ae dependent of z. In FIG. 2, in which the plane on drawing coincides with the plane P"e of FIG. 1, this mosaic M thus comprises $m$ columns ($c1, c2, \ldots cm$) and ($2r + 1$) rows, i.e. the row of transmitters 1l and 2r rows of 1e receivers 11A, 12A, ... 1rA and 11B,12B, ... 1rB which are symmetrically arranged with respect to the row of transmitters. In the embodiment shown, the number of transmission transducers equal the number of columns $m$, and each column comprises one transmission transducer. Obviously, other arrangments are alternatively possible.

The receive transducers of each column are connected to $r$ terminals $t1, t2 \ldots tr$, each terminal being connected to two receive transducers which are symmetrically arranged with respect to the transmission transducers of the relevant column. These two receive transducers (for example, $r1A(1)$ and $r1B(1)$) together constitute a receive element, so that the mosaic comprises $r \times m$ receive elements, each of which is characterized by a column number (1 to $m$) and by a row number (1 to $r$).

FIG. 2 also shows a control unit B which supplies:

synchronization pulses s, in reaction to which a generator G transmits the ultrasonic pulse series iu at time intervals T;

a signal ae (transmitter address) by means of which a selection circuit DA successively selects the transmission transducers el . . . em in order to transfer $r$ ultrasonic pulses to each of these transmission transducers (i.e. a number of pulses which equals the number of terminals per column, or the number of double rows of the mosaic);

a signal al (row address) by means of which selection circuits MA1 to MAm, associated with the $m$ columns, actuate receive elements which are situated in one row, for example, row $d$ of the mosaic, during the time interval T which follows the application of an ultrasonic pulse iu to a transmission transducer; each transmission transducer thus successively receives $r$ ultrasonic pulses, and each time the receive elements connected to one of the terminals $t1$ to $tr$ (terminal $td$ in the example) are actuated;

a signal ac (column address) by means of which an ultra-fast selection circuit DU, coupled to the outputs of the analog selection circuits MA1 to MAm, successively actuates, during each of the S sub-intervals T/S of the time interval T which follows an ultrasonic pulse of the order $d$ which is applied to a transmission transducer of the order $e$, the receive elements which are situated in the mosaic in row $d$ and in $q$ columns which are situated on both sides of the column containing the transmission transducer of the order $e$.

Thus the first transmitter e1 is pulsed $r$ times (the same number $r$ as the number of receive elements, each receive element comprising two receive transducers), then the second transmitter e2 is pulsed $r$ times, and so on until the last transmitter em is pulsed $r$ times. Each pulse is spaced by a time interval T. This time interval T is divided into S sub-intervals. During the first sub-interval following the first pulse of e1, a scan is made of receive elements in the first row (comprising receive transducers $r1A(l) \ldots r1A(m)$ and $r1B(l) \ldots r1B(m)$ in parallel). During the second subinterval following the first pulse of e1 a second scan is made of the same elements and so forth until a predetermined number of scans of these elements have been made. During the first sub-interval following the second pulse of e1, a scan is made of the second row of receive elements (comprising receive transducers $r2A(l) \ldots r2A(m)$ and $r2B(l) \ldots r2B(m)$ in parallel). During the second sub-interval following the second pulse of e1 a second scan is made of the same elements of the second row and so forth for a predetermined number of scans. After $r$ pulses of e1, the first pulse of e2 is again followed by a predetermined number of scans of fthe first row of receive elements and the second pulse of e2 followed by a predetermined number of scans of the second row of receive elements, etc.

Figure 4:
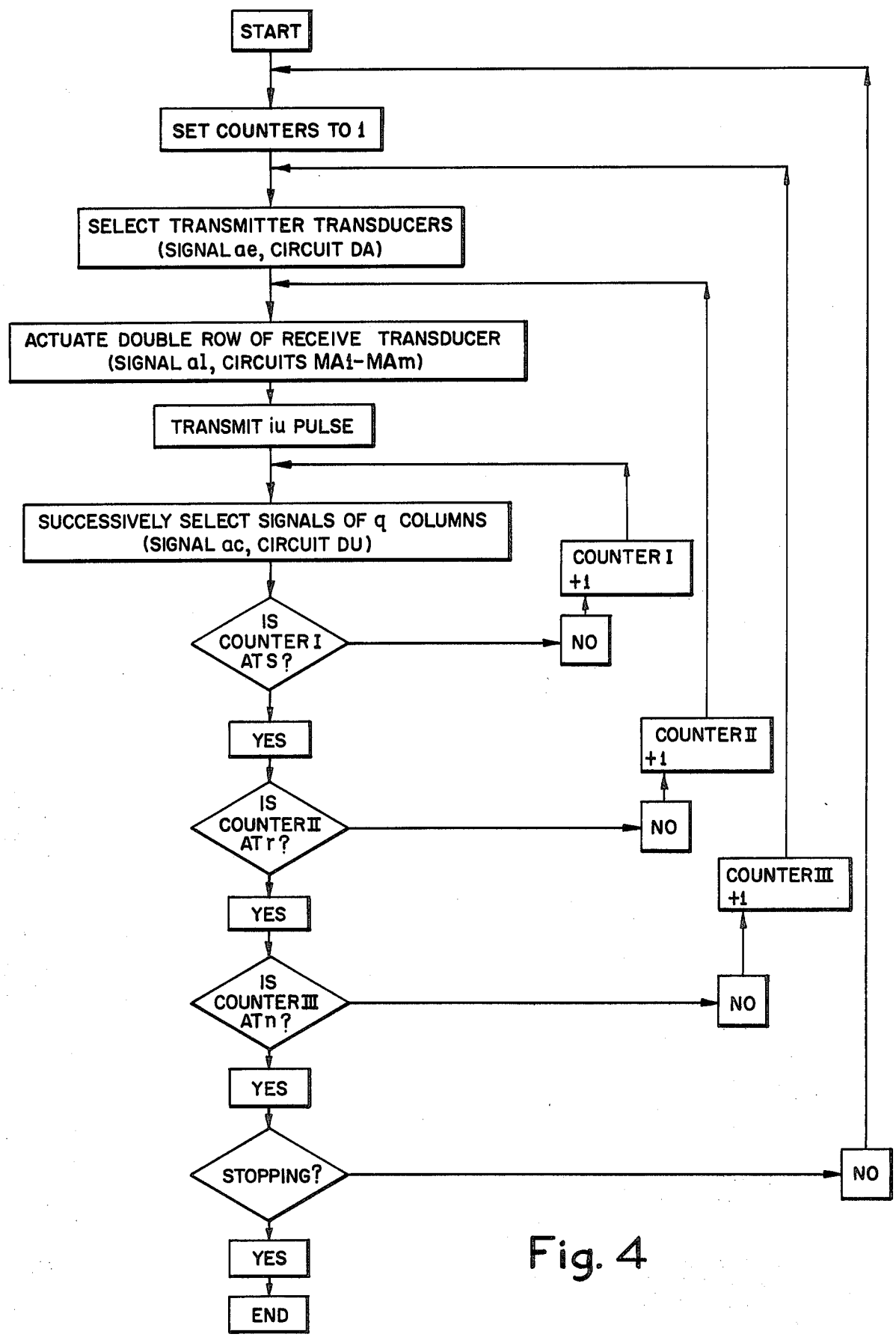
FIG. 4 is a flow chart of the sequential operation.

The described procedure is diagramatically shown in FIG. 4 which is self-explanatory. Using counters I, II and III (not shown in FIG. 2), the number of times that the various scans must be repeated can be checked. Counter I counts the scans of the same row following a pulse transmission. When the counter I is at S, the number of sub-intervals S have expired, a second pulse has been transmitted and the second row must be scanned. Counter II advances to keep track of the row being scanned so that when the rth row has been scanned the counter III will advance and keep track of the transmission element being actuated. When the last transmission element has been pulsed r times and the last row of receive elements has been scanned s times follow the rth pulse of the last transmission element, the sequence may be repeated or not depending upon any arbitrary criterion embodied in the "stopping" element.

The synchronization pulses s and the signals ae, al, ac are applied to a calculating unit C which supplies a cathode-ray tube (not shown) with signals for scanning the screen of the tube in the X-direction and the Y-direction. The scanning in the X-direction is effected with a period T/S, while the deflection $h$ in the Y-direction satisfies the expression:

$$h = \sqrt{\frac{c^2t^2 - x^2 - y^2)^2 - 4x^2y^2}{2 ct}}$$

wherein:

c is the velocity of the sound in the relevant medium, $t$ is the time period since transmission of the last synchronized pulse $iu$ $x$ is the distance between on the one side the transmission transducer which is controlled by this pulse $iu$ and on the other side the column which contains the actuated receive element $y$ is the distance between the row of transmission tranducers and the row which contains the actuated receive element.

The signals selected by the ultra-fast selection circuit DU are applied to the control electrode W of the cathode ray tube; this electrode normally blocks the electron beam in the tube and unblocks it when signals are applied to this electrode which signify the reception of an echo signal at the area of the actuated receive element.

FIG. 4 reveals that the image constructed in the cathode-ray tube by the electron beam for each transmission transducer consists of $r$ groups of S scans each which extend in the X-direction. The width of the image represents the distance between the two ends of the $q$ actuated columns. Each of the rxS scans follows a path in the y-direction determined by the formula for $h$ heretofore described.

The S lines of a group are scanned between two transmitted pulses $iu$, i.e. during the interval T. Each next line displays echo signals of a depth greater than that of the previous one, because more time has expired since the transmission of the first of the said pulses $iu$; zero depth (the first line) corresponds to an echo from the plane $P''e$ which contains the row of transmission transducers. The value $r$ (number of double lines of receive transducers) determines the limits between which the inclination lies of the interfaces causing the reception of an echo signal. The progress in the X-direction in FIG. 1, caused by the successive selection of the transmission transducers el . . . em, results in the complete scanning of an image which corresponds to the portion of the plane P in which the examined section of the body to be examined is situated. It will be obvious that the image is composed of lines, each of which corresponds to a small portion of a tangent to the surface portion which caused the echo signal.

Figure 3:
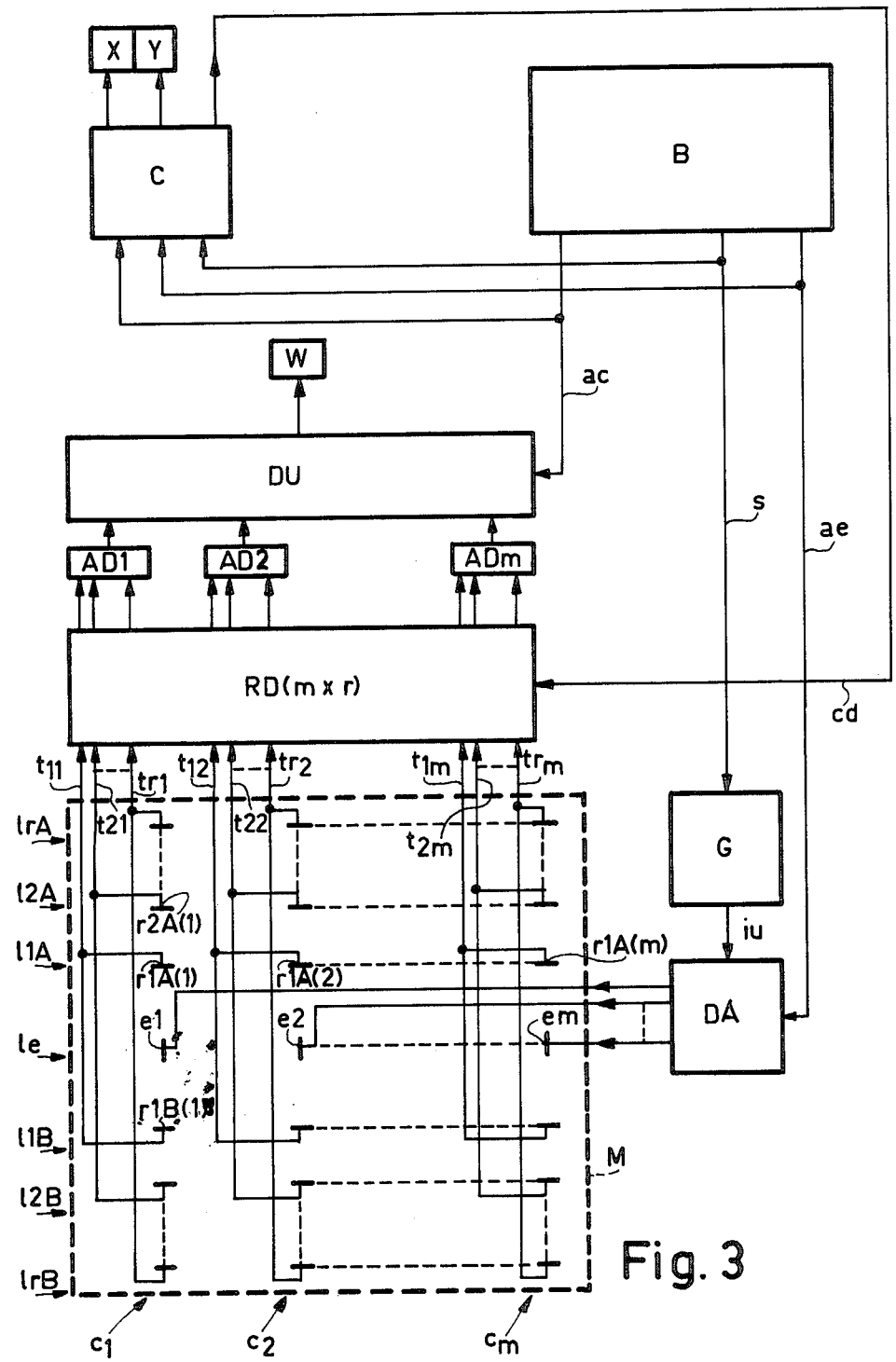
FIG. 3 shows a further embodiment of the arrangement of FIG. 2.

FIG. 3 diagrammatically shows a variant. The principle thereof will first be described. This variant simplifies the signal processing, because it enables either only a single scan to be performed for the receive transducers of the various rows, or the simultaneous processing of the receiver signals for which $x$ has the same value while $y$ has different values. To this end it is necessary to determine the function $\Delta t\ (t,x,y)$ which is such that $$h\ (t - \Delta t,\ x,y) = h(t,x,y_o) \qquad (2)$$

so that, when the signal is delayed by an amount $t$, it may be considered to originate from row $y_o$. The scanning of the screen of the cathode-ray tube then satisfies the expression $$h = f(c,t,x,y_o)$$

and the echo signals of all rows are simultaneously displayed.

The above equation (2) cannot be rigorously realized, but it is possible to find a $\Delta t$ function by means of which the equality can be adequately approximated taking into account the resolution of ultrasonic systems.

According to the results of a calculation model, the following values can be chosen for $y_o$ and $\Delta t$:

$$y_o = 0, \text{ and}$$

$$\Delta t = y^2/\sigma^2 t.$$

FIG. 3 shows a few circuits which correspond to circuits shown in FIG. 2 and which are denoted by the same references, i.e. the control unit B, the calculating unit C, the ultra-fast selection circuit DU, the ultrasonic generator G, and the selection circuit DA.

At the output of the mosaic M the terminals $t11$ . . . $trm$ are connected to an assembly of $(m \times r)$ phase shift registers RD, i.e. one register for each receive element. The phase shift registers are controlled by a phase shift signal which is supplied by the calculating unit C. The receive signals originating from one column simultaneously appear on the output of the phase shift registers associated with the receive elements of the relevant column. The outputs of these registers are connected to the inputs of summing device AD1 for column 1, AD2 for column 2, . . . AD$m$ for column $m$. The selection of the various columns is effected by means of the selection circuit DU in the same manner as in FIG. 2.

In FIG. 4 this means that after the transmission of a single pulse $iu$ by the selected transmission transducers, actuation sequences of $q$ columns each take place (checked by counter I; not changed); however, this is effected after the simultaneous actuation of all rows of a column, so that the counting of the number of double rows (counter II) is eliminated.

Taking into account given restrictions (number of images displayed on the screen of the cathode-ray tube per second, sampling period for the selection circuit DU, detection depth etc.), the invention can be realized, for example, in the form of a mosaic comprising 24 transmission transducers, 24 columns and 4 double rows. The number of $q$ selected columns is, for example, 15, so there are 7 columns on both sides of the column containing the controlled transmission transducer.

Maximum receive time after each transmission; 200 $\mu$s, followed by a dead time of 300 $\mu$s to avoid parasitic echo signals caused by multiple reflections.

time for constructing a complete image: 48 ms (so slightly more than 20 images per second).

For both described embodiments of the system according to the invention the value 200 was chosen for the number of actuation sequences S, and 1$\mu$s was chosen as the duration of each sequence.

What is claimed is:

1. A device for ultrasonic examination of a body situated in an analysis plane, comprising:
   a plurality of transmission transducers situated in a row lying in the analysis plane and having a direction of transmission in the analysis plane toward the body:
   means for pulsing the transmission transducers one at a time in a predetermined spaced sequence for launching ultrasonic pulses therefrom toward the body;
   a plurality of receive transducers situated in each of a plurality of parallel planes which are perpendicular to the row of transmission transducers, the receive transducers being oriented to detect echo pulses reflected from interfaces in the body;
   means for determining the depth of an interface, connected to receive signals from said receive transducers, which function to determine the depth of an interface reflecting an echo pulse with respect to the row of transducers from the time of detection of the echo pulse and the position of the detecting receive transducer with respect to the position of the transmission transducer that launched the detected pulse; and means for displaying, connected to receive signals representing the depth of the interface from the means for determining the depth, which function to display detected echo pulses as image points on a screen, the positions of image points in one rectangular coordinate direction corresponding to the positions of the receive transducers detecting the corresponding echo pulses along the direction of the row of transmission transducers and in the other rectangular coordinate direction corresponding to the determined depths of the reflective interfaces, the image points together forming an image of the reflective interfaces of the body which intersect the analysis plane.

2. A device as defined in claim 1 wherein the receive transducers lie in a plane which also contains the row of transmission transducers, the plane being perpendicular to the analysis plane.

3. A device as defined in claim 2 wherein the receive transducers are arranged in an even number of rows parallel to the row of transmission transducers and symmetrical therewith and each symmetrical pair of receive transducers are electrically connected together as a single receive element.

* * * * *